(12) United States Patent
Jordan et al.

(10) Patent No.: US 7,700,500 B2
(45) Date of Patent: Apr. 20, 2010

(54) DURABLE HYDROPHILIC TREATMENT FOR A BIODEGRADABLE POLYMERIC SUBSTRATE

(75) Inventors: Joy Francine Jordan, Marietta, GA (US); Ali Yahiaoui, Roswell, GA (US); Palani Raj Ramaswami Wallajapet, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 656 days.

(21) Appl. No.: 10/734,004

(22) Filed: Dec. 10, 2003

(65) Prior Publication Data

US 2004/0127123 A1 Jul. 1, 2004

Related U.S. Application Data

(60) Provisional application No. 60/436,086, filed on Dec. 23, 2002.

(51) Int. Cl.
*B32B 27/04* (2006.01)
(52) U.S. Cl. ........................................ 442/79; 428/359
(58) Field of Classification Search ................ 442/79, 442/85, 86, 361, 400, 401; 428/359
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,471,597 A | 10/1969 | Schirmer | |
| 3,502,763 A | 3/1970 | Hartmann | |
| 3,542,615 A | 11/1970 | Dobo et al. | |
| 3,692,618 A | 9/1972 | Dorschner et al. | |
| 3,754,117 A | 8/1973 | Walter | |
| 3,802,817 A | 4/1974 | Matsuki et al. | |
| 3,849,241 A | 11/1974 | Butin et al. | |
| 3,855,046 A | 12/1974 | Hansen et al. | |
| 3,880,966 A | 4/1975 | Zimmerman et al. | |
| D239,566 S | 4/1976 | Vogt | |
| 4,100,324 A | 7/1978 | Anderson et al. | |
| 4,283,291 A | 8/1981 | Lowther | |
| D264,512 S | 5/1982 | Rogers | |
| 4,340,563 A | 7/1982 | Appel et al. | |
| 4,374,888 A | 2/1983 | Bornslaeger | |
| 4,493,868 A | 1/1985 | Meitner | |
| 4,818,464 A | 4/1989 | Lau | |
| 5,102,738 A | 4/1992 | Bell et al. | |
| 5,108,820 A | 4/1992 | Kaneko et al. | |
| 5,108,827 A | 4/1992 | Gessner | |
| 5,112,690 A | 5/1992 | Cohen et al. | |
| 5,258,221 A | 11/1993 | Meirowitz et al. | |
| 5,294,482 A | 3/1994 | Gessner | |
| 5,336,552 A | 8/1994 | Strack et al. | |
| 5,338,822 A | 8/1994 | Gruber et al. | |
| 5,350,624 A | 9/1994 | Georger et al. | |
| 5,382,400 A | 1/1995 | Pike et al. | |
| 5,556,895 A | 9/1996 | Lipinsky et al. | |
| 5,614,295 A | 3/1997 | Quincy, III et al. | |
| 5,618,298 A | 4/1997 | Simon | |
| 5,700,559 A | 12/1997 | Sheu et al. | |
| 5,759,926 A | 6/1998 | Pike et al. | |
| 5,801,223 A | 9/1998 | Lipinsky et al. | |
| 5,807,636 A | 9/1998 | Sheu et al. | |
| 5,814,567 A * | 9/1998 | Yahiaoui et al. ............ 442/118 |
| 5,858,515 A | 1/1999 | Stokes et al. | |
| 5,972,176 A | 10/1999 | Kirk et al. | |
| 5,976,694 A * | 11/1999 | Tsai et al. ................... 428/373 |
| 6,011,194 A * | 1/2000 | Buglino et al. ................ 602/41 |
| 6,051,249 A * | 4/2000 | Samuelsen .................. 424/443 |
| 6,111,060 A | 8/2000 | Gruber et al. | |
| 6,200,669 B1 | 3/2001 | Marmon et al. | |
| 6,201,068 B1 * | 3/2001 | Tsai et al. ................... 525/178 |
| 6,268,434 B1 * | 7/2001 | Tsai et al. ................... 525/178 |
| 6,353,086 B1 | 3/2002 | Kolstad et al. | |
| 6,440,556 B2 * | 8/2002 | Matsui et al. ................ 428/370 |
| 6,506,873 B1 * | 1/2003 | Ryan et al. .................. 528/354 |
| 2002/0111596 A1 * | 8/2002 | Fletcher et al. ......... 604/385.03 |
| 2004/0127123 A1 * | 7/2004 | Jordan et al. .................. 442/76 |
| 2005/0002981 A1 * | 1/2005 | Lahtinen et al. ............. 424/423 |
| 2005/0136155 A1 * | 6/2005 | Jordan et al. .................. 426/77 |
| 2005/0267560 A1 * | 12/2005 | Bates ......................... 623/1.1 |

FOREIGN PATENT DOCUMENTS

| | | |
|---|---|---|
| EP | 0125851 | 11/1984 |
| EP | 0603784 A1 | 6/1994 |

(Continued)

OTHER PUBLICATIONS

Abstract, JP 01192871 A, Aug. 2, 1989, Nonoguchi et al.

(Continued)

*Primary Examiner*—Arti Singh-Pandey
(74) *Attorney, Agent, or Firm*—Dority & Manning, P.A.

(57) ABSTRACT

The present invention relates to a biodegradable substrate having a durable hydrophilic surface prepared from a biodegradable polymeric substrate having a surface, wherein the biodegradable polymeric substrate has been rendered hydrophilic by subjecting the substrate to a corona glow discharge and/or coating the substrate with a hydrophilic polymeric material in an amount of from about 0.01 to about 2.0 percent by weight, based on the dry weight of the substrate. The biodegradable substrate can be used in absorbent personal care product, biomedical devices and food packaging.

24 Claims, 1 Drawing Sheet

FOREIGN PATENT DOCUMENTS

| | | |
|---|---|---|
| EP | 0484830 B1 | 8/1995 |
| EP | 0815879 | 1/1998 |
| EP | 1022363 A1 | 7/2000 |
| EP | 1051956 A1 | 11/2000 |
| EP | 1057915 A1 | 12/2000 |
| EP | 1270650 | 1/2003 |
| EP | 1312702 A1 | 5/2003 |
| WO | WO 95/19796 | 7/1995 |
| WO | WO 97/05193 | 2/1997 |
| WO | WO 97/11834 | 4/1997 |
| WO | WO 97/47801 | 12/1997 |
| WO | WO 98/50611 | 11/1998 |
| WO | WO 99/01099 | 1/1999 |
| WO | WO 00/19955 | 4/2000 |
| WO | WO 00/51566 | 9/2000 |
| WO | WO 01/51545 | 7/2001 |
| WO | WO 01/57306 | 8/2001 |
| WO | WO 01/78865 A1 | 10/2001 |
| WO | WO 02/15955 | 2/2002 |

OTHER PUBLICATIONS

Abstract, JP 2000080559 A, Mar. 21, 2000, Yamashita et al.

Catoire, B. et al., "Physico-chemical modifications of superficial regions of low-density polyethylene (LDPE) film under corona discharge", *Polymer*, vol. 25, pp. 766-772, Jun. 1984.

Pitt, W.G., "Fabrication of a Continuous Wettability Gradient by Radio Frequency Plasma Discharge", *Journal of Colloid and Interface Science*, vol. 133, No. 1, Nov. 1989, pp. 223-227.

Lee, J.H. et al., "Wettability Gradient Surfaces Prepared by Corona Discharge Treatment", The 17$^{th}$ Annual Meeting of the Society for Biomaterials, May 1-5, 1991, Scottsdale, AZ, p. 133.

Khang, G. et al., "Interaction of fibroblast cells on poly(lactide-co-glycolide) surface with wettability chemogradient", *Bio-Medical Materials and Engineering*, 9, 1999, pp. 179-187.

Walsh, D. et al., "Preparation of porous composite implant materials by in situ polymerization of porous apatite containing ϵ-caprolactone or methyl methacrylate", *Biomaterials*, 22, 2001, pp. 1205-1212.

\* cited by examiner

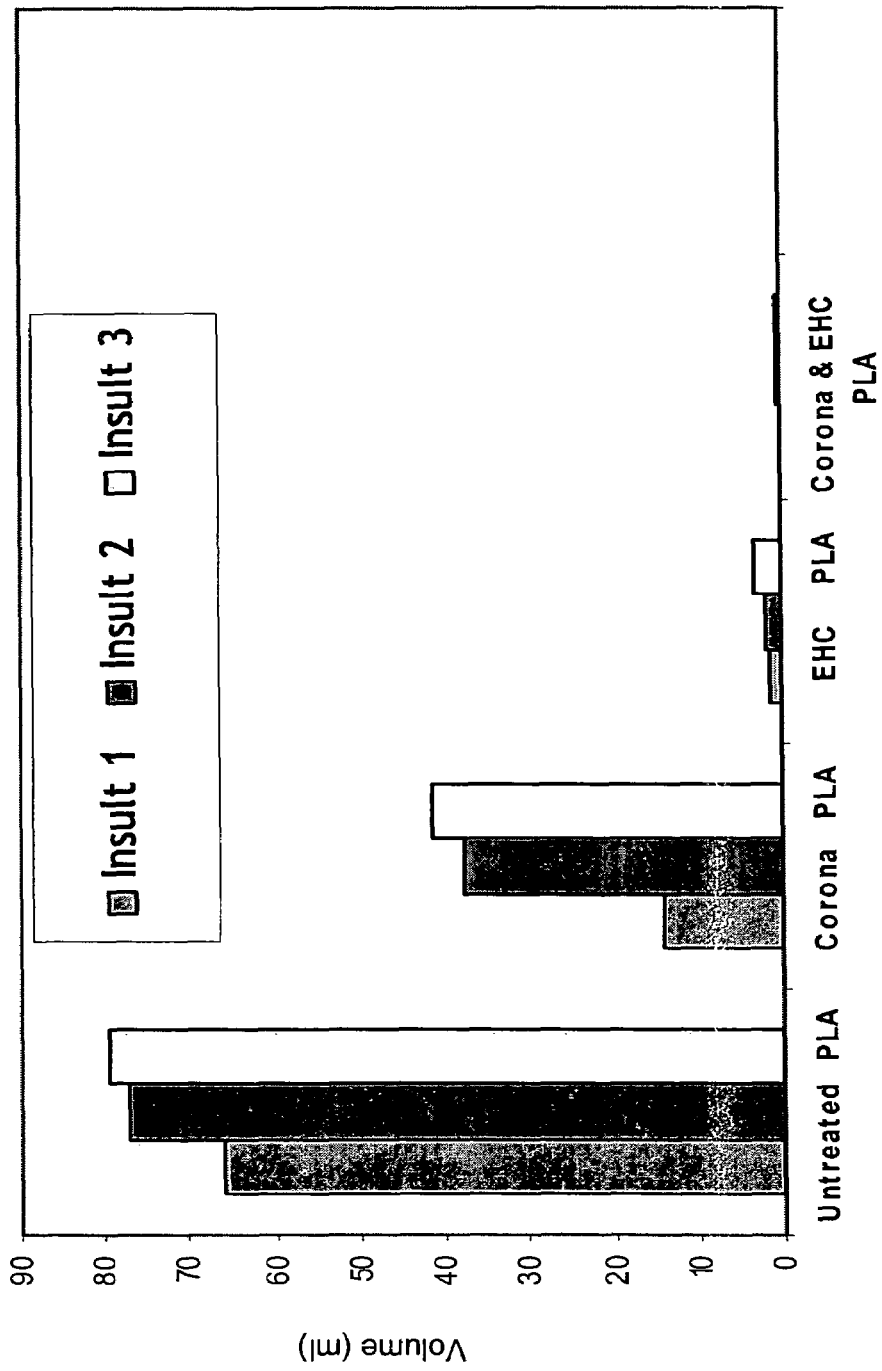
FIGURE

DURABLE HYDROPHILIC TREATMENT FOR A BIODEGRADABLE POLYMERIC SUBSTRATE

This application claims priority from U.S. Provisional Application No. 60/436,086 filed Dec. 23, 2002.

FIELD OF THE INVENTION

The present invention relates to a biodegradable polymeric substrate which has been rendered hydrophilic by subjecting the substrate to a durable hydrophilic treatment.

BACKGROUND OF THE INVENTION

Polymers are used extensively to make a variety of products which include blown and cast films, extruded sheets, injection molded articles, foams, blow molded articles, extruded pipe, monofilaments, and nonwoven webs. Some of such polymers, such as polyolefins, are naturally hydrophobic, and for many uses this property is either a positive attribute or at least not a disadvantage. There are a number of uses for polymers, however, where their hydrophobic nature either limits their usefulness or requires some effort to modify the surface characteristics of the shaped articles made therefrom.

By way of example, polyolefins, such as polyethylene and polypropylene, are used to manufacture polymeric fabrics which are employed in the construction of such disposable absorbent articles as diapers, feminine care products, incontinence products, training pants, wipes, and the like. Such polymeric fabrics often are nonwoven webs prepared by, for example, such processes as meltblowing, coforming, and spunbonding. Frequently, such polymeric fabrics need to be wettable by water or aqueous-based liquids. Wettability can be obtained by spraying or otherwise coating (i.e., surface treating or topically treating) the fabric with a surfactant solution during or after its formation, and then drying the web.

Some of the more common topically applied surfactants are nonionic surfactants, such as polyethoxylated octylphenols and condensation products of propylene oxide with propylene glycol, by way of illustration only. These surfactants are effective in rendering normally hydrophobic polymeric fabrics water wettable. However, the surfactant is readily removed from the fabric, often after only a single exposure to an aqueous liquid. Such surfactants are effective in rendering the hydrophobic polymeric fabric wettable by lowering the surface tension of the aqueous liquid. Such a mechanism must involve at least partial removal of surfactant from the surfaces of the fibers of which the fabric is composed.

Other methods of improving wettability of polymers include methods such as corona discharge, plasma discharge, plasma jet, flame treatment, acid etching, or any method that can oxidize the surface of the substrate. However, as is known in the art, wettability introduced by these methods degenerates after treatment, as is disclosed in U.S. Pat. No. 5,700,559 to Sheu et al.

Nonwoven webs have been used to prepare a wide variety of products, including personal care products such as disposable diapers, training pants, feminine care products, baby wipes and the like. Nonwoven webs have also been used to prepare many other articles of manufacture including health care products, such as surgical drapes, surgical mask, wound dressings and the like; wipes; mops; filter materials, among many other uses.

Many of the items prepared from nonwoven webs are single use or limited use products. Most of the current nonwoven webs are prepared from polymers which are not considered biodegradable, such as polyolefins. Although currently available disposable baby diapers and other disposable products have been accepted by the public despite the fact that they are not biodegradable, these current products would benefit from improvement in the area of disposal.

Solid waste disposal is becoming an ever increasing problem throughout the world. As landfills continue to fill-up, a demand has increased for a material source reduction in disposable products. As an alternative, recyclable or biodegradable components are needed to be developed for incorporating into the disposable products. Products are needed to be developed for final disposal by means other than by incorporation into solid waste disposal facilities such as landfills.

There is a need for new materials to be used in disposable products which retain integrity and strength during use, but after such use, the materials may be disposed of more efficiently. There is a need for new materials used in the disposable product to be disposed of easily and efficiently by composting. Alternatively, the disposable product may be disposed of easily and efficiently in a liquid sewage system wherein the disposable product is capable of being degraded.

Attempts have been made to overcome some of the environmental short comings of the current disposable products by using biodegradable polymers such as aliphatic polyesters as the polymer component used to make the nonwoven web. Aliphatic polyesters, like polyolefins, are typically hydrophobic, or have a low degree of wettablility.

In addition, the use of biodegradable polymeric substrates in other applications including biomedical devices such as sutures and scaffolds for tissue regeneration has become increasingly popular. In these applications, there is a need for the biodegradable polymeric substrates to be hydrophilic and rendered hydrophilic in a manner which is safe for users of these products.

Accordingly, there is a need for a biodegradable polymeric substrate having a durable hydrophilic treatment that is stable during storage, that is biodegradable and that is wettable by water without significantly lowering the surface tension of an aqueous medium to which the coated substrate may be exposed.

SUMMARY OF THE INVENTION

The present invention relates to a biodegradable substrate having a durable hydrophilic surface prepared from a biodegradable polymeric substrate having a surface, wherein the biodegradable polymeric substrate has been subjected to a corona glow discharge to render the surface hydrophilic. It has be unexpectedly discovered that the biodegradable polymeric substrate may be rendered hydrophilic by subjecting the substrate prepared to a corona glow discharge and that the treatment is durable, remaining effective even after extended storage periods. By way of example, the substrate may be a single fiber, a fibrous material, a film or a sheet-like material, such as a sheet of a foamed material. The sheet-like material also may be a fibrous web, such as a woven or nonwoven fabric or web. The fibrous web desirably will be a nonwoven web.

Another aspect of the present invention addresses some of the challenges and problems of providing a wettable and durable hydrophilic coating on a biodegradable polymeric substrate. The surfaces of the substrate are substantially uniformly coated with a biodegradable hydrophilic polymeric coating material. The biodegradable polymeric substrate, may be, by way of illustration only, an aliphatic polyester. For example, the aliphatic polyester may be a polylactide, a polylactic acid or a polyglycolic acid among others. The coating of the biodegradable hydrophilic polymeric material is durable under a wide range of temperatures up to and including about 90° C. Moreover, the coating of the hydrophilic polymeric material does not significantly suppress the surface tension of an aqueous medium with which the substrate may come in contact. In certain embodiments, the hydrophilicity of the coating of polymeric material will vary in a controlled manner across at least one dimension of the substrate. By way of example, the substrate may be a sheet-like material, such as a sheet of a foamed material. The sheet-like material also may be a fibrous web, such as a woven or nonwoven fabric or web. The fibrous web desirably will be a nonwoven web.

Also by way of example, the hydrophilic biodegradable polymeric coating material may be a polysaccharide. As another example, the polymeric material may be a modified polysaccharide. When the hydrophilic polymeric material is a polysaccharide, it may have a plurality of hydrophobic groups and a plurality of hydrophilic groups. The hydrophobic groups may be =CH— and —CH2- groups in the polysaccharide backbone. The hydrophobic groups may be adapted to provide an affinity of the hydrophilic biodegradable polymeric material for the biodegradable polymer substrate and the hydrophilic groups may be adapted to render the polymeric material hydrophilic.

When the hydrophilic biodegradable polymeric coating material is a modified polysaccharide, the hydrophobic groups may be =CH— and —CH2- groups in the polysaccharide backbone or pendant groups. The hydrophilic groups also may be pendant groups. For example, the modified polysaccharide may be, by way of example only, a modified cellulose. For example, the hydrophobic groups may be pendant monovalent alkyl groups, such as ethyl groups. As another example, the hydrophilic groups may be pendant monovalent hydroxyalkyl groups, such as hydroxyethyl groups.

The treated substrate of the present invention may be used as a component of a disposable absorbent product. Examples of disposable absorbent products include, by way of illustration only, diapers; training pants; feminine care products, such as sanitary napkins and tampons; incontinent care products; surgical gowns; surgical drapes; wipes; in food applications such as tea bags; in biodegradable biomedical material such as sutures, filters, scaffolds for tissue regeneration and reconstructive surgery.

The durable hydrophilic surface on biodegradable polymeric substrate is prepared by a method of providing a biodegradable polymeric substrate; and subjecting the substrate to a corona glow discharge to impart a durable hydrophilic surface to the biodegradable polymeric substrate. In an additional method of producing the durable hydrophilic surface on biodegradable polymeric substrate is accomplished by coating the biodegradable polymeric substrate with a biodegradable hydrophilic polymeric material.

BRIEF DESCRIPTION OF THE DRAWINGS

The FIGURE shows the data from the run-off test shown from Example 3.

DEFINITIONS

As used herein, the term "comprising" is inclusive or open-ended and does not exclude additional unrecited elements, compositional components, or method steps.

As used herein, the term "biodegradable polymeric substrate" is meant to include any shaped article, provided it is and composed, in whole or in part, of a biodegradable polymer which is hydrophobic, or has a low degree of wettability. For example, the substrate may be a sheet-like material, such as a sheet of a film or a foamed material. The sheet-like material also may be a fibrous web, such as a woven or nonwoven fabric or web. The substrate also may include biodegradable polymer fibers, per se, or biodegradable polymer fibers which have been formed into a fibrous web. The fibrous web desirably will be a nonwoven web, such as, but not limited to, a meltblown web, a spunbonded web, a bonded carded web, or an air-laid web. The substrate also may be a laminate of two or more layers of a sheet-like material. For example, the layers may be independently selected from the group consisting of meltblown webs, a spunbond webs, a bonded carded webs, and an air-laid webs. However, other sheet-like materials may be used in addition to, or instead of, meltblown webs, spunbond webs, bonded carded webs, or air-laid webs. In addition, the layers of the laminate may be prepared from the same biodegradable polymer or different biodegradable polymers.

The biodegradable polymer of the substrate also may contain minor amounts of additives as is customary in the art. For example, the biodegradable polymer may contain pigments, fillers, delustrants, antioxidants, antistatic agents, stabilizers, oxygen scavengers, and the like.

As used herein, the term "hydrophilic biodegradable polymeric coating material" means that the biodegradable polymeric material has a surface free energy such that the polymeric material is wettable by an aqueous medium. That is, an aqueous medium wets the hydrophilic polymeric material with which the substrate is coated. For example, the surface free energy of the hydrophilic polymeric material may be at least about 50 dynes/cm. As another example, the surface free energy of the hydrophilic polymeric material may be in a range of from about 50 to about 72 dynes/cm.

As used herein, "biodegradable" is meant to represent that a material degrades from the action of naturally occurring microorganisms such as bacteria, fungi, algae and the like. "Biodegradable" also is intended to include a material which degrades in the presence of oxygen over an extended period of time.

The term "durable" as used herein with reference to a coating of a biodegradable polymeric substrate means that the treated substrate retains its hydrophilic nature even after storage for extended periods of time, for example at least 1 month. In addition, the term durable also means that the treated substrate remains wettable after at least three exposures to an aqueous medium, such as water, saline, and urine and other body fluids.

One procedure for evaluating durability when the substrate is a fibrous web is a liquid absorbency time test. In this test, a 5 gram sample of a material is places in a 8 cm high, 5 cm in diameter wire cage cylinder prepared from a wire of a suitable gauge so that the cylinder weighs 3 g. A 5 gram sample of the nonwoven web is placed inside the cage. The cage and the material are dropped into room temperature water and the time for the basket to sink is measured. The full test procedure is outlined in ISO-9373

Another procedure for evaluating durability when the substrate is a fibrous web is a modified run-off test followed by washing and drying (a wash/dry cycle). The fibrous web typically will remain wettable for at least five cycles of exposing, washing, and drying. Desirably, the coated substrate will remain wettable after being subjected to at least ten cycles.

The run-off test (exposure) and wash/dry procedure are described in U.S. Pat. No. 5,258,221 to Meirowitz et al. which is incorporated herein by reference. Typically, a generally rectangular, 8-inch by 15-inch (about 20-cm by 38-cm) sample of a fibrous web, such as a nonwoven web, is mounted on top of an absorbent core composed of polypropylene, wood pulp fibers, and/or a superabsorbent material. The resulting test assembly is centered on the inclined surface and held in place with tape at each corner of the assembly. The angle of the inclined surface is 45° instead of the 30° angle described in the patent. The funnel is located at approximately 7.8 inches (about 200 mm) from the bottom or lower edge of the test assembly. The valve of the funnel is located approximately 10 mm above the top surface of the test assembly. One hundred ml of water having a temperature of 35° C. is placed in the funnel. The valve of the funnel is opened to dispense the water over a period of about 15 seconds. The amount of water which runs off and is collected in the collection means is determined and recorded. A fibrous web is typically considered to pass the modified run-off test if the amount of water collected in the collection means is less than an amount deemed appropriate for a given type of fibrous web. For example, when the fibrous web is a lightweight (e.g., having a basis weight of 0.6 ounces per square yard or about 20 grams per square meter) spunbonded nonwoven web, the amount of water collected should be less than 20 ml.

The wash/dry cycle was modified by utilizing 500 ml, rather than one liter, of room-temperature water (about 23° C.). Thus, the generally rectangular sample of coated substrate described above is placed in the 500 ml of water. The sample is allowed to remain in the water for one minute while being agitated at 15-20 revolutions per minute by a mechanical shaker. The sample is removed from the water and excess liquid squeezed back into the wash water container. The sample is allowed to air dry overnight and then is subjected to the modified run-off test described above. This process is repeated the desired number of times. The surface tension of the wash water is determined after each wash/dry cycle with fresh water being used for each cycle. The surface tension of the water is determined according to ASTM Test Method D 1590-60 using a Fisher tensiometer (Fisher Scientific Company, Pittsburgh, Pa.).

The term "aqueous medium" is used herein to mean any liquid medium of which water is a major component. Thus, the term includes water per se and aqueous solutions and dispersions. For example, the aqueous medium may be a liquid bodily discharge, such as urine, menses, and saliva.

As used herein, the term "wettable" and variations thereof means wettable by an aqueous medium, i.e., the aqueous medium spreads over the surface of a substrate. The term is used interchangeably with the term "wettable by water" and variations thereof and has the same meaning.

As used herein, the phrase "affinity of the polymeric material for the biodegradable polymer substrate" means that the hydrophilic polymeric material coats the substrate substantially uniformly (i.e., to an extent sufficient to permit the coated substrate to be wet by an aqueous medium), typically after first exposing the substrate to a field of reactive species. The term "partial affinity" means that the polymeric material partially coats the substrate. The functional consequence of a partial affinity is that the coated substrate is only partially wettable.

The term "monovalent alkyl group" is used herein to mean a monovalent alkyl group having from 1 to about 6 carbon atoms. Examples of monovalent alkyl groups include, by way of illustration only, methyl, ethyl, 1-propyl, isopropyl, 1 butyl, 2-butyl, t-butyl, 1-pentyl, 2-pentyl, 3-pentyl, 2-methyl-2-butyl, 3-methyl-2-butyl, 1-hexyl, 2-hexyl, 3-hexyl, 4-hexyl, 2,2-dimethylbutyl, 2,3-dimethylbutyl, 2-methylpentyl, 3-methylpentyl, 3-ethyl-2-butyl, and the like.

As used herein, the term "monovalent hydroxyalkyl group" means a monovalent alkyl group as described above in which a hydrogen atom has been replaced with a hydroxy group. Examples of monovalent hydroxyalkyl groups include, also by way of illustration, hydroxyethyl, 2-hydroxypropyl, 3-hydroxypropyl, 1-hydroxy-2-propyl, 4-hydroxybutyl, 3-hydroxybutyl, 2-hydroxybutyl, 4-hydroxy-2-butyl, 3-hydroxy-2-butyl, 2-hydroxymethyl-2-propyl, 5-hydroxypentyl, 4-hydroxypentyl, 3-hydroxypentyl, 2-hydroxypentyl, 5-hydroxy-2-pentyl, 4-hydroxy-2-pentyl, 3-hydroxy-2-pentyl, 5-hydroxy-3-pentyl, 4-hydroxy-3-pentyl, 2-hydroxymethyl-2-butyl, 3-hydroxymethyl-2-butyl, 3-methyl-1-hydroxy-2-butyl, 6-hydroxyhexyl, 4hydroxy-2-hexyl, 1-hydroxy-3-hexyl, 2-hydroxy-4-hexyl, 2,2-dimethyl-4-hydroxybutyl, 2,3-dimethyl-1-butyl, 2-hydroxymethylpentyl, 2-methyl-4-hydroxypentyl, 3-(2-hydroxyethyl)2-butyl, and the like.

The term "pendant" is used herein with respect to the monovalent alkyl and hydroxyalkyl groups to mean that such groups are attached to the polymer backbone but are not part of it. Thus, removal of the pendant groups will not alter the chemical structure of the backbone.

As used herein, the term "fiber" includes both staple fibers, i.e., fibers which have a defined length between about 19 mm and about 60 mm, fibers longer than staple fiber but are not continuous, and continuous fibers, which are sometimes called "substantially continuous filaments" or simply "filaments". The method in which the fiber is prepared will determine if the fiber is a staple fiber or a continuous filament.

As used herein, the term "nonwoven web" means a web having a structure of individual fibers or threads which are interlaid, but not in an identifiable manner as in a knitted web. Nonwoven webs have been formed from many processes, such as, for example, meltblowing processes, spunbonding processes, air-laying processes, coforming processes and bonded carded web processes. The basis weight of nonwoven webs is usually expressed in ounces of material per square yard (osy) or grams per square meter (gsm) and the fiber diameters useful are usually expressed in microns, or in the case of staple fibers, denier. It is noted that to convert from osy to gsm, multiply osy by 33.91.

As used herein the term "spunbond web" refers to a nonwoven web prepared from small diameter fibers of molecularly oriented polymeric material. Spunbond fibers may be formed by extruding molten thermoplastic material as filaments from a plurality of fine, usually circular capillaries of a spinneret with the diameter of the extruded filaments then being rapidly reduced as in, for example, U.S. Pat. No. 4,340, 563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al, and U.S. Pat. No. 5,382,400 to Pike et al. Spunbond fibers are generally not tacky when they are deposited onto a collecting surface and are generally continuous. Spunbond fibers are often about 10 microns or greater in diameter. However, fine fiber spunbond webs (having an average fiber diameter less than about 10 microns) may be achieved by various methods including, but not limited to, those described in commonly assigned U.S. Pat. No. 6,200,669 to Marmon et al. and U.S. Pat. No. 5,759, 926 to Pike et al., each is hereby incorporated by reference in its entirety.

As used herein, the term "meltblown web" refers to a nonwoven web formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, which is hereby incorporated by reference in its entirety. Meltblown fibers are microfibers, which may be continuous or discontinuous, and are generally smaller than 10 microns in average diameter The term "meltblown" is also intended to cover other processes in which a high velocity gas, (usually air) is used to aid in the formation of the filaments, such as melt spraying or centrifugal spinning.

As used herein, the term "coform nonwoven web" or "coform material" means composite materials comprising a mixture or stabilized matrix of thermoplastic filaments and at least one additional material, usually called the "second material" or the "secondary material". As an example, coform materials may be made by a process in which at least one meltblown die head is arranged near a chute through which the second material is added to the web while it is forming. The second material may be, for example, an absorbent material such as fibrous organic materials such as woody and non-wood pulp such as cotton, rayon, recycled paper, pulp fluff; superabsorbent materials such as superabsorbent particles and fibers; inorganic absorbent materials and treated polymeric staple fibers and the like; or a non-absorbent material, such as non-absorbent staple fibers or non-absorbent particles. Exemplary coform materials are disclosed in commonly assigned U.S. Pat. No. 5,350,624 to Georger et al.; U.S. Pat. No. 4,100,324 to Anderson et al.; and U.S. Pat. No. 4,818,464 to Lau et al.; the entire contents of each is hereby incorporated by reference.

"Bonded carded web" refers to webs that are made from staple fibers which are sent through a combing or carding unit, which separates or breaks apart and aligns the staple fibers in the machine direction to form a generally machine direction-oriented fibrous nonwoven web. Such fibers are usually purchased in bales which are placed in an opener/blender or picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" or "airlaid" is a well known process by which a fibrous nonwoven layer can be formed. In the airlaying process, bundles of small fibers having typical lengths ranging from about 3 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

As used herein, the term "multicomponent fibers" refers to fibers or filaments which have been formed from at least two polymers extruded from separate extruders but spun together to form one fiber. Multicomponent fibers are also sometimes referred to as "conjugate" or "bicomponent" fibers or filaments. The term "bicomponent" means that there are two polymeric components making up the fibers. The polymers are usually different from each other, although conjugate fibers may be prepared from the same polymer, if the polymer in each component is different from one another in some physical property, such as, for example, melting point or the softening point. In all cases, the polymers are arranged in substantially constantly positioned distinct zones across the cross-section of the multicomponent fibers or filaments and extend continuously along the length of the multicomponent fibers or filaments. The configuration of such a multicomponent fiber may be, for example, a sheath/core arrangement, wherein one polymer is surrounded by another, a side-by-side arrangement, a pie arrangement or an "islands-in-the-sea" arrangement. Multicomponent fibers are taught in U.S. Pat. No. 5,108,820 to Kaneko et al.; U.S. Pat. No. 5,336,552 to Strack et al.; and U.S. Pat. No. 5,382,400 to Pike et al.; the entire content of each is incorporated herein by reference. For two component fibers or filaments, the polymers may be present in ratios of 75/25, 50/50, 25/75 or any other desired ratios.

As used herein, the term "multiconstituent fibers" refers to fibers which have been formed from at least two polymers extruded from the same extruder as a blend or mixture. Multiconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Fibers of this general type are discussed in, for example, U.S. Pat. Nos. 5,108,827 and 5,294,482 to Gessner.

As used herein, the term "pattern bonded" refers to a process of bonding a nonwoven web in a pattern by the application of heat and pressure or other methods, such as ultrasonic bonding. Thermal pattern bonding typically is carried out at a temperature in a range of from about 80° C. to about 180° C. and a pressure in a range of from about 150 to about 1,000 pounds per linear inch (59-178 kg/cm). The pattern employed typically will have from about 10 to about 250 bonds/inch$^2$ (1-40 bonds/cm$^2$) covering from about 5 to about 30 percent of the surface area. Such pattern bonding is accomplished in accordance with known procedures. See, for example, U.S. Design Pat. No. 239,566 to Vogt, U.S. Design Pat. No. 264,512 to Rogers, U.S. Pat. No. 3,855,046 to Hansen et al., and U.S. Pat. No. 4,493,868 to Meitner et al. and U.S. Pat. No. 5,858,515 to Stokes et al., for illustrations of bonding patterns and a discussion of bonding procedures, which patents are incorporated herein by reference. Ultrasonic bonding is performed, for example, by passing the multilayer nonwoven web laminate between a sonic horn and anvil roll as illustrated in U.S. Pat. No. 4,374,888 to Bornslaeger, which is hereby incorporated by reference in its entirety.

DETAILED DESCRIPTION

The biodegradable polymeric substrate of the present invention is prepared from a biodegradable polymer which is hydrophobic or has a low degree of wettablility. It is desirable to render the biodegradable polymeric substrate hydrophilic in many applications.

In the present invention, the biodegradable polymers used to produce the substrate include biodegradable aliphatic polyester polymers. Examples of biodegradable aliphatic polyesters usable in the present invention include, but are not limited to polyhydroxy butyrate (PHP), polyhydroxy butyrate-covalerate (PHBV), polycaprolactane, polybutylene succinate, polybutylene succinate-co-adipate, polyglycolic acid (PGA), polylactide or polylactic acid (PLA), polybutylene oxalate, polyethylene adipate, polyparadioxanone, polymorpholineviones, and polydioxipane-2-one. Of these aliphatic polyesters, polyglycolic acid and polylactide (polylactic acid) are desirable due to the availability and recent manufacturing advances. Due to current cost considerations, polylactide (polylactic acid) is most desired.

Polylactides are sometimes referred to as polylactic acid. As used herein, the term polylactide is intended to cover both polylactides and polylactic acid. Polylactides are often abbreviated "PLA". Polylactide polymers are commercially available from Cargill-Dow LLC, Minnetonka, Minn., for example, 6200 D grade as described by EP 1 312 702 A1, from PURAC America, Lincolnshire, Ill. and from Biomer, Krailling Germany. Polylactides are also described in U.S. Pat. Nos. 5,338,822; 6,111,060; 5,556,895; 5,801,223; 6,353,086; and 6,506,873, each hereby incorporated by reference in its entirety.

As is mentioned above, the biodegradable polymeric substrate may be a sheet-like material, such as a sheet of a film or a foamed material. The sheet-like material also may be a fibrous web, such as a woven or nonwoven fabric or web. The substrate also may include polymer fibers, per se, or polymer fibers which have been formed into a fibrous web. The fibrous web desirably will be a nonwoven web, such as, but not limited to, a meltblown web, a spunbonded web, a bonded carded web, or an air-laid web. The substrate also may be a laminate of two or more layers of a sheet-like material. For example, the layers may be independently selected from the group consisting of meltblown webs, spunbond webs, bonded carded webs, and air-laid webs. However, other sheet-like materials may be used in addition to, or instead of, meltblown webs, spunbond webs, bonded carded webs, or air-laid webs. In addition, the layers of the laminate may be prepared from the same biodegradable polymer or different biodegradable polymers.

When the substrate is a nonwoven web, the fibers of the nonwoven web layer may be monocomponent fibers, meaning fibers prepared from one polymer component, multiconstituent fibers, or multicomponent fibers. The multicomponent fibers may, for example, have either of an A/B or A/B/A side-by-side cross-sectional configuration, a sheath-core cross-sectional configuration, wherein one polymer component surrounds another polymer component, a pie cross-sectional arrangement or and island-in sea arrangement. Each of the polymers of the multicomponent fibers may be biodegradable, or one may be biodegradable and the other may not be biodegradable. More than two components may be used as well.

The biodegradable polymeric substrate may be rendered hydrophilic with a durable hydrophilic treatment by one of two methods. In a first method of the present invention, the biodegradable polymeric substrate is rendered hydrophilic by subjecting the substrate to a corona glow discharge. In this method, the biodegradable polymeric substrate having a surface is subjected to a corona glow discharge to render the surface hydrophilic.

Corona glow discharge treatments of polymeric films is known in the art and results in a chemical modification of the polymers in the surface of the polymeric material. See for example U.S. Pat. No. 3,880,966 to Zimmerman et al., U.S. Pat. No. 3,471,597 to Schirmer Corona discharge treatment of films is also old in the art and it is known that corona discharge treatment of a polymer film in the presence of air entails substantial morphological and chemical modifications in the polymer film's surface region. See Catoire et al, "Physico-chemical modifications of superficial regions of low-density polyethylene (LDPE) film under corona discharge," Polymer, vol. 25, p. 766, et. seq, June, 1984.

Generally speaking, corona treatment has been utilized to either (1) improve the print fastness on the film, or (2) to perforate the film. For example, U.S. Pat. No. 4,283,291 to Lowther describes an apparatus for providing a corona discharge, and U.S. Pat. No. 3,880,966 to Zimmerman et al discloses a method of using a corona discharge to perforate a crystalline elastic polymer film and thus increase its permeability. U.S. Pat. No. 3,471,597 to Schirmer also discloses a method for perforating a film by corona discharge. U.S. Pat. No. 3,754,117 to Walter discloses an apparatus and method for corona discharge treatment for modifying the surface properties of thin layers or fibers which improve the adhesion of subsequently applied inks or paints or of subsequent bonding.

In the present invention, the biodegradable polymeric substrate is exposed to a corona field. As used herein, the term "corona field" means a corona field of ionized gas. In general, the generation of a corona field and exposure of the fibers are accomplished in accordance with procedures which are well known to those having ordinary skill in the art. The dose or energy density to which the fibers are exposed can range from about 1 to about 500 watt-minute per square foot (w-min/ft2), which is approximately equivalent to a range of from about 0.6 to about 323 kilojoules per square meter (kJ/m2). Desirably, such dose will be in a range of from about 15 to about 350 w-min/ft2 (from about 10 to about 226 kJ/m2). Most desirably, dose will be in a range of from about 20 to about 80 w-min/ft2 (from about 13 to about 52 kJ/m2). Desirably, the corona glow discharge treatment is applied to the substrate under ambient temperature and pressure; however, higher or lower temperature and pressures may be used.

In a second method of the present invention, the biodegradable polymeric substrate is rendered hydrophilic with a durable hydrophilic treatment by coating onto the substrate, a hydrophilic polymeric material which is durable to an aqueous medium at a temperature in a range of from about 10° C. to about 90° C. and does not significantly suppress the surface tension of an aqueous medium with which the fibrous web may come in contact. For example, the surface tension of the aqueous medium may not be suppressed or lowered more than about 10 percent.

By way of illustration only, the hydrophilic polymeric material may be a polysaccharide. The polysaccharide may have a plurality of hydrophobic groups and a plurality of hydrophilic groups. The hydrophobic groups may be =CH— and —CH2- groups in the polysaccharide backbone. The hydrophobic groups may be adapted to provide an affinity of the polymeric coating material for biodegradable polymeric substrate and the hydrophilic groups may be adapted to render the polymeric material hydrophilic. Examples of polysaccharides include, for example, natural gums, such as agar, agarose, carrageenans, furcelleran, alginates, locust bean gum, gum arabic, guar gum, gum konjac, and gum karaya; microbial fermentation products, such as gellan gum, xanthan gum, and dextran gum; cellulose, such as microcrystalline cellulose; and animal products, such as hyaluronic acid, heparin, chitin, and chitosan.

Again by way of illustration only, the hydrophilic polymeric material may be a modified polysaccharide. A modified polysaccharide also may have a plurality of hydrophobic groups and a plurality of hydrophilic groups. The hydrophobic groups may be =CH— and —CH2- groups in the polysaccharide backbone, or pendant groups. The hydrophilic groups also may be pendant groups. Again, the hydrophobic groups may be adapted to provide an affinity of the biodegradable polymeric substrate and the hydrophilic groups may be adapted to render the polymeric material hydrophilic. By way of illustration only, examples of modified polysaccharides include modified celluloses or cellulose derivatives, such as hydroxyethyl cellulose, hydroxypropyl cellulose, methyl cellulose, ethyl cellulose, methyl hydroxypropyl cellulose, ethyl hydroxyethyl cellulose, and carboxymethyl cellulose; starch and pectin derivatives, such as carboxymethyl starch, starch aldehyde, and pectates; and animal product derivatives, such as carboxymethyl chitin and carboxymethyl chitosan.

Particularly useful types of polysaccharides and modified polysaccharides include, by way of illustration, agar; alginates; and modified celluloses, such as ethyl hydroxyethyl cellulose. In modified polysaccharides, particularly in the useful type of modified polysaccharides just noted, the hydrophobic groups may be pendant monovalent alkyl groups. For example, such hydrophobic groups may be methyl or ethyl groups. As a further example, the hydrophilic groups may be pendant monovalent hydroxyalkyl groups. As yet another example, such hydrophilic groups may be hydroxyethyl groups.

Finally, the hydrophilicity of the coating of polymeric material may vary in a controlled manner across at least one dimension of the coated substrate, commonly referred to as a "zone treatment". For example, a coated substrate may have a central region of higher hydrophilicity which extends, for example, along the length of the substrate, with regions of lower hydrophilicity on both sides of the central region. Thus, the hydrophilicity of such a substrate would vary in a controlled manner across the width thereof. Other variations coming within the scope of the present invention will be readily apparent to those having ordinary skill in the art.

Turning now to the method for preparing a coated substrate, the method involves providing a biodegradable polymeric substrate and optionally exposing at least a portion or all of the substrate to a field of reactive species. At least a portion of the substrate, including any portion exposed to the field of reactive species, then is treated with a mixture which includes water and a hydrophilic polymeric material as described above under conditions sufficient to substantially uniformly coat the surfaces of the substrate with the hydrophilic polymeric material. Any conventional treating method, for example, spraying, applying a foam, printing, dipping and the like, may be used to coat the substrate. The coating of the hydrophilic polymeric material is durable to an aqueous medium at a temperature in a range of from about 10° C. to about 90° C. and the coating does not significantly depress the surface tension of an aqueous medium with which the coated substrate may come in contact. For example, the surface tension depression of such an aqueous medium may be less than about 10 percent. In some instances, it may be either helpful or necessary to crosslink the coating on the substrate to impart a desired level of durability.

The field of reactive species serves to increase the affinity of the hydrophilic polymeric material for the biodegradable polymeric substrate. The field of reactive species may be, by way of example, a corona field. As another example, the field of reactive species may be a plasma field.

As an alternative method, the coating may first be applied to the substrate and then the substrate may be subjected to a reactive species field.

Without wishing to be bound by theory, it is believed that exposure of the biodegradable polymer substrate to a field of reactive species results in alterations of the surfaces of the substrate, thereby temporarily raising the surface energy of the substrate. This, in turn, allows the penetration of the treating solution into the substrate; that is, the substrate may be saturated with the treating solution. It is also believed that the durability of the treatment is due to surface oxidation and enhanced secondary bonding of a hydrophilic coating which may be applied to the substrate.

Although exposure of the substrate to a field of reactive species is a desired method of temporarily raising the surface energy of the substrate, other procedures may be employed. For example, the substrate may be treated with ozone or passed through an oxidizing solution, such as an aqueous medium containing chromium trioxide and sulfuric acid. Care should be taken with such other procedures, however, to either prevent or minimize degradation of the substrate.

The strength of the field of reactive species may be varied in a controlled manner across at least one dimension of the fibrous web. Upon coating the substrate with the hydrophilic polymeric material, the extent or degree of hydrophilicity of the coating is directly proportional to the strength of the field. Thus, the hydrophilicity of the coating of polymeric material will vary in a controlled manner across at least one dimension of the fibrous web.

The strength of the field of reactive species is readily varied in a controlled manner by known means. For example, a corona apparatus having a segmented electrode may be employed, in which the distance of each segment from the sample to be treated may be varied independently. As another example, a corona apparatus having a gap-gradient electrode system may be utilized; in this case, one electrode may be rotated about an axis which is normal to the length of the electrode. Other methods also may be employed; see, for example, "Fabrication of a Continuous Wettability Gradient by Radio Frequency Plasma Discharge", W. G. Pitt, J. Colloid Interface Sci., 133, No. 1, 223 (1989); and "Wettability Gradient Surfaces Prepared by Corona Discharge Treatment", J. H. Lee, et al., Transactions of the 17th Annual Meeting of the Society for Biomaterials, May 1-5, 1991, page 133, Scottsdale, Ariz.

If desired, at least a portion of the biodegradable polymeric substrate may be exposed to a field of reactive species subsequent to treating at least a portion of the substrate with a mixture comprising water and a polymeric material. Such post-exposure typically increases the hydrophilicity of the coated substrate. Moreover, the strength of the field of reactive species in such post-exposure also may vary in a controlled manner across at least one dimension of the fibrous web as already described. Such post-exposure may even enhance the durability of the coating through crosslinking.

Typically, the add-on amount of the hydrophilic polymer in the coating applied to the substrate is generally in the range of about 0.01 wt % to about 2.0 wt %, and desirably between 0.05 wt % and 1.0 wt %, most desirably between about 0.1 wt % and about 0.5 wt %, each based on the dry weight of the substrate and hydrophilic polymer in the coating.

The methods described above for render the biodegradable polymer hydrophilic. In addition to being durable, the methods may provide a coating which is food safe and can be used in food storage products as well as in medical devices which are used on and in the human body, although this has not been confirmed. The treatments of the present invention impart fast wettability, durability during storage, durability during use which allows for rewetting of the surface after a first insult, have efficacy at elevated temperatures, are tasteless, are non-foaming and are food safe, such as in the case for ethyl hydroxyl cellulose coatings. Surprisingly, it has been discovered that the corona treatment of the biodegradable polymeric substrate results in a substrate which retains its imparted hydrophilic properties even after storage for an extended period of time.

The present invention is further described by the examples which follow. Such examples, however, are not to be construed as limiting in any way either the spirit or the scope of the present invention.

Example 1

Polylactic acid available from Cargill-Dow, LLC, 6200 D grade, was formed into a spunbond fabric using conventional spunbond apparatus of the type described in U.S. Pat. No. 3,802,817 to Matsuki et al. The resulting spunbond fabric has filaments of an average denier of about 1.8 dpf (2.0 dtex) and a basis weight of about 0.5 osy (about 17 gsm). The resulting fabric was cut into two portions, with one portions of the fabric being left untreated for control purposes and the second portion of the fabric was exposed to a corona glow discharge under ambient conditions, the field strength was about 20 watts/ft$^2$/min (about 1.33 J/cm2). Each sample was aged for three months and tested for wettability using the sink test method in accordance with ISO-9073, which is briefly described above.

A 5 gram sample of the corona treated fabric and 5 gram untreated fabric were placed in 25° C. water. The treated fabric sank in 0.5 seconds and the untreated fabric sank in about 180 seconds.

A 5 gram sample e of the corona treated fabric and 5 gram untreated fabric were stored at ambient conditions for a period of three months. After the storage period, each sample of the fabric was placed in 25° C. water. The stored treated fabric also sank in 0.5 seconds, and the untreated fabric did not sink after three minutes. This result shows that the corona treatment of the fabric retained the hydrophilic nature even after three months of storage at ambient conditions.

Example 2

Polylactic acid available from Cargill-Dow, LLC, 6200 D grade was formed into a spunbond fabric using conventional spunbond apparatus as used in Example 1. The resulting spunbond fabric has filaments of an average denier of about 1.6 dpf (1.8 dtex) and a basis weight of about 0.5 osy (about 17 gsm). A portion of the fabric was left untreated for control purposes and a portion of the fabric was exposed to a corona glow discharge under ambient conditions. The field strength was about 20 watts/ft$^2$/min (about 1.33 J/cm2). Immediately following the corona treatment, the fabric was dipped into one of three aqueous solutions containing 0.1 wt %, 0.2 wt % or 0.3 wt. % of ethyl hydroxyethyl cellulose (Bermocol E481, Akzo Nobel), forming fabrics A, B, C. After complete saturation of the fabric, indicated by a change in color from white to translucent, the fabric was nipped between two rubber rollers in an Atlas laboratory wringer at 10 lbs (about 4.5 kg) nip pressure. The coated fabric then was dried in an oven at 60° C. for about 30 minutes.

Each sample was then tested for wettability using the test method in accordance with ISO-9073, which is described above.

The sink time for each of the treated fabrics was measured as was the sink time for the untreated fabric by a 5 gram sample of the treated fabric and 5 gram sample of the untreated fabric were placed in 25° C. water. The sink times are shown in Table 1.

| | Sample | | | |
|---|---|---|---|---|
| | Untreated | A | B | C |
| Sink time | 59.3 seconds | 3.6 seconds | 3.0 seconds | 3.0 seconds |

As can be seen in Table 1, the treated fabric has faster sink times as compared to the untreated fabric.

Example 3

A 0.5 osy (17 gsm) polylactic acid spunbond was formed from a polylactic acid available from Cargill-Dow, LLC, 6200 D grade, using conventional spunbond apparatus as in Example 1. The resulting spunbond fabric had filaments of an average denier of about 2.0 dpf (2.2 dtex). The resulting fabric was cut into portions, with one portion being left untreated as a control and three other portions being treated as follows.

Sample 1—A portion of the fabric was treated with a corona glow discharge under ambient conditions. The field strength was about 20 watts/ft$^2$/min (about 1.33 J/cm$^2$).

Sample 2—A portion of the fabric was dipped into one of three aqueous solutions containing 0.2 wt % of ethyl hydroxyethyl cellulose (Bermocol E481, Akzo Nobel), forming fabrics A, B, C. After complete saturation of the fabric, indicated by a change in color from white to translucent, the fabric was nipped between two rubber rollers in an Atlas laboratory wringer at 10 lbs (about 4.5 kg) nip pressure. The coated fabric then was dried in an oven at 60° C. for about 30 minutes.

Sample 3—A portion of the fabric was treated with a corona glow discharge under ambient conditions. The field strength was about 20 watts/ft$^2$/min (about 1.33 J/cm$^2$). Immediately following the corona treatment, the fabric was dipped into one of three aqueous solutions containing 0.2 wt % of ethyl hydroxyethyl cellulose (Bermocol E481, Akzo Nobel), forming fabrics A, B, C. After complete saturation of the fabric, indicated by a change in color from white to translucent, the fabric was nipped between two rubber rollers in an Atlas laboratory wringer at 10 lbs (about 4.5 kg) nip pressure. The coated fabric then was dried in an oven at 60° C. for about 30 minutes.

The effectiveness and durability of the treatments in making the fabric hydrophilic was tested using the inclined run-off test. In this test, rectangular strips of the spunbond fabric were cut to the dimensions of 16 inches long and 4.5 inches wide. The web was placed on an absorbent material of identical dimensions composed of 58% wood pulp (CR 1654 available from Bowater Inc., Coosa Pines, Ala.) and 42% superabsorbent (Favor SXM 880 available from Stockhausen Inc., Greensboro, N.C.) densified to 0.2 grams/cc with average basis weight of about 800 grams per square meter. The spunbond fabric was placed in contact with the absorbent on a 30 degree inclined plastic sheet. A funnel was placed in the vertical position along the centerline of the fabric about 2 cm from the top edge, with the tip of the funnel about 1 cm form the surface of the fabric. 100 milliliters of water at a temperature of about 35° C. was added through the funnel to impact the web at an angle of 60 degrees. The water that penetrated the fabric was absorbed by the absorbent layer underneath and the water that ran-off the fabric without penetrating was collected in a beaker at the bottom of the inclined board and measured to obtain the run-off volume for the first insult. The fabric was then removed, dried in air for 30 minutes under ambient conditions and the test repeated to obtain the fluid run-off for the second insult. This procedure was repeated once more to obtain the fluid run-off for the third insult.

The results of the testing are shown in the FIGURE. The fluid run-off volume can be used as a measure of the effectiveness of the hydrophilic treatment. A more hydrophilic surface will result in a smaller fluid run-off volume compared to a less hydrophilic surface Comparison of the fluid run-off collected from the three insults provides information on durability of the treatment. A more durable treatment will have a smaller fluid run-off volume with multiple insults compared to a less durable treatment. As can be seen from the data the fluid run-off volume for the treated fabrics are more hydrophilic compared to the untreated fabric and the treatments are also durable.

While the specification has been described in detail with respect to specific embodiments thereof, it will be appreciated that those skilled in the art, upon attaining an understanding of the foregoing, may readily conceive of alterations to, variations of, and equivalents to these embodiments.

What is claimed is:

1. A biodegradable fibrous web comprising biodegradable polymer fibers, wherein the biodegradable polymer fibers comprise polylactic acid, the web having a durable hydrophilic surface coated with a hydrophilic polymeric material in an amount of from about 0.01 to about 2.0 percent by weight, based on the dry weight of the web; in which the hydrophilic polymeric material is a cellulose derivative, the cellulose derivative selected from the group consisting of hydroxyethyl cellulose, hydroxypropyl cellulose, methyl cellulose, ethyl cellulose, methyl hydroxypropyl cellulose, ethyl hydroxyethyl cellulose, carboxymethyl cellulose, or a combination thereof; wherein the hydrophilic polymeric material will not significantly suppress the surface tension of an aqueous medium with which the web may come in contact.

2. The biodegradable fibrous web of claim 1, wherein the hydrophilic polymeric material comprises from about 0.05 to about 1.0 percent by weight of the web, based on the dry weight of the web.

3. The biodegradable fibrous web of claim 2, wherein the hydrophilic polymeric material comprises from about 0.1 to about 0.5 percent by biodegradable fibrous web of claim 1.

4. An absorbent personal care product comprising the biodegradable fibrous web of claim 1.

5. The biodegradable fibrous web of claim 1, wherein the web is a nonwoven web.

6. The biodegradable fibrous web of claim 5, wherein the nonwoven web is a meltblown web, spunbond web, or a combination thereof.

7. The biodegradable fibrous web of claim 1, wherein the surface is substantially uniformly coated with the hydrophilic polymeric material.

8. The biodegradable fibrous web of claim 1, wherein the cellulose derivative is ethyl hydroxyethyl cellulose.

9. A biomedical device comprising a biodegradable fibrous web, the biodegradable fibrous web comprising biodegradable polymer fibers, wherein the biodegradable polymer fibers comprise polylactic acid, the web having a durable hydrophilic surface coated with a hydrophilic polymeric material in an amount of from about 0.01 to about 2.0 percent by weight, based on the dry weight of the web; in which the hydrophilic polymeric material is a cellulose derivative, the cellulose derivative selected from the group consisting of hydroxyethyl cellulose, hydroxypropyl cellulose, methyl cellulose, ethyl cellulose, methyl hydroxypropyl cellulose, ethyl hydroxyethyl cellulose, carboxymethyl cellulose, or a combination hereof; wherein the hydrophilic polymeric material will not significantly suppress the surface tension of an aqueous medium with which the web may come in contact.

10. The biomedical device of claim 9, wherein the biomedical device is selected from the group consisting of sutures, filters, and scaffolds.

11. The biomedical device of claim 9, wherein the hydrophilic polymeric material comprises from about 0.05 to about 1.0 percent by weight of the web, based on the dry weight of the web.

12. The biomedical device of claim 11, wherein the hydrophilic polymeric material comprises from about 0.1 to about 0.5 percent by biodegradable fibrous web of claim 1.

13. The biomedical device of claim 9, wherein the web is a nonwoven web.

14. The biomedical device of claim 13, wherein the nonwoven web is a meltblown web, spunbond web, or a combination thereof.

15. The biomedical device of claim 9, wherein the surface is substantially uniformly coated with the hydrophilic polymeric material.

16. The biomedical device of claim 9, wherein the cellulose derivative is ethyl hydroxyethyl cellulose.

17. A food package comprising a biodegradable fibrous web, the biodegradable fibrous web comprising biodegradable polymer fibers, wherein the biodegradable polymer fibers comprise polylactic acid, the web having a durable hydrophilic surface coated with a hydrophilic polymeric material in an amount of from about 0.01 to about 2.0 percent by weight, based on the dry weight of the web; in which the hydrophilic polymeric material is a cellulose derivative, the cellulose derivative selected from the group consisting of hydroxyethyl cellulose, hydroxypropyl cellulose, methyl cellulose, ethyl cellulose, methyl hydroxypropyl cellulose, ethyl hydroxyethyl cellulose, carboxymethyl cellulose, or a combination thereof; wherein the hydrophilic polymeric material will not significantly suppress the surface tension of an aqueous medium with which the web may come in contact.

18. The food package of claim 17, wherein food package is a tea bag.

19. The food package of claim 17, wherein the hydrophilic polymeric material comprises from about 0.05 to about 1.0 percent by weight of the web, based on the dry weight of the web.

20. The food package of claim 19, wherein the hydrophilic polymeric material comprises from about 0.1 to about 0.5 percent by biodegradable fibrous web of claim 1.

21. The food package of claim 17, wherein the web is a nonwoven web.

22. The food package of claim 21, wherein the nonwoven web is a meltblown web, spunbond web, or a combination thereof.

23. The food package of claim 17, wherein the surface is substantially uniformly coated with the hydrophilic polymeric material.

24. The food package of claim 17, wherein the cellulose derivative is ethyl hydroxyethyl cellulose.

* * * * *